United States Patent
O'Halloran et al.

(10) Patent No.: US 11,260,029 B2
(45) Date of Patent: Mar. 1, 2022

(54) FISH FEED COMPOSITIONS CONTAINING A NEONICOTINOID FOR PREVENTING AND TREATING PARASITE INFECTIONS

(71) Applicants: John O'Halloran, Old Ridge (CA); John Terence Drost, Douglas (CA)

(72) Inventors: John O'Halloran, Old Ridge (CA); John Terence Drost, Douglas (CA)

(*) Notice: Subject to any disclaimer, the term of this patent is extended or adjusted under 35 U.S.C. 154(b) by 657 days.

(21) Appl. No.: 15/321,896

(22) PCT Filed: Jun. 24, 2015

(86) PCT No.: PCT/IB2015/054749
§ 371 (c)(1),
(2) Date: Dec. 23, 2016

(87) PCT Pub. No.: WO2015/198247
PCT Pub. Date: Dec. 30, 2015

(65) Prior Publication Data
US 2017/0135956 A1    May 18, 2017

Related U.S. Application Data

(60) Provisional application No. 62/016,389, filed on Jun. 24, 2014.

(51) Int. Cl.
| | |
|---|---|
| *A61K 31/4439* | (2006.01) |
| *A61K 31/44* | (2006.01) |
| *A61K 31/5395* | (2006.01) |
| *A61K 31/341* | (2006.01) |
| *A61K 47/42* | (2017.01) |
| *A23K 20/10* | (2016.01) |
| *A23K 10/30* | (2016.01) |
| *A23K 50/80* | (2016.01) |
| *A61K 9/16* | (2006.01) |
| *A61K 9/00* | (2006.01) |
| *A23K 20/158* | (2016.01) |

(52) U.S. Cl.
CPC ............ *A61K 9/167* (2013.01); *A23K 10/30* (2016.05); *A23K 20/10* (2016.05); *A23K 20/158* (2016.05); *A23K 50/80* (2016.05); *A61K 9/0053* (2013.01); *A61K 9/1617* (2013.01); *A61K 9/1658* (2013.01); *A61K 31/341* (2013.01); *A61K 31/44* (2013.01); *A61K 31/4439* (2013.01); *A61K 31/5395* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 4,886,656 | A | 12/1989 | Obayashi et al. |
| 5,504,081 | A * | 4/1996 | Lohr .................. A01N 43/40 |
| | | | 514/225.2 |
| 57,122,951 | | 1/1998 | Mencke et al. |
| 6,054,454 | A | 4/2000 | Schmid et al. |
| 6,083,520 | A | 7/2000 | Toneby |
| 8,257,763 | B2 | 9/2012 | Va Wijnoogst et al. |
| 8,968,817 | B2 * | 3/2015 | Kobler ................. C07C 319/20 |
| | | | 426/656 |
| 2008/0194641 | A1 | 8/2008 | Anspaugh et al. |
| 2009/0148589 | A1 * | 6/2009 | Fox ........................ A23J 1/005 |
| | | | 426/648 |
| 2010/0137134 | A1 | 6/2010 | Gewehr et al. |
| 2010/0254959 | A1 | 10/2010 | Lahm et al. |
| 2011/0152177 | A1 | 6/2011 | Vecino et al. |
| 2011/0183012 | A1 | 7/2011 | Gewehr et al. |

FOREIGN PATENT DOCUMENTS

| | | |
|---|---|---|
| EP | 407343 B1 | 6/1997 |
| EP | 1915056 A2 | 4/2008 |
| EP | 2178378 B1 | 1/2013 |
| WO | 9721350 A1 | 6/1997 |
| WO | 2007019176 A2 | 2/2007 |
| WO | 2014064184 A1 | 5/2014 |

OTHER PUBLICATIONS

Federal Register/vol. 75, No. 81 Apr. 28, 2010 rules and regulations (Year: 2010).*
International Search Report received in connection to International patent application No. PCT/IB2015/054749, dated Oct. 30, 2015.
Truscott, E. et al., "Identifying Optimal Threshold Statistics for Elimination of Hookworm Using A Stochastic Simulation Model", Parasites & Vectors, 2017, 10:321 (Abstract Only).
Whyte, S.K., et al., "Comparison of the Depletion of Emamectin Benzoate (SLICE) Residues From Skeletal Muscle and Skin of Atlantic Salmon (*Salmor salar*), for Multiple Dietary Dose Regimens at 10° C.", Aquaculture, May 21, 2011, vol. 315, Issues 3-4, pp. 228-235.

* cited by examiner

*Primary Examiner* — Alton N Pryor
(74) *Attorney, Agent, or Firm* — Bereskin & Parr LLP

(57) ABSTRACT

The present disclosure relates to methods of preventing or treating parasite infection in a plurality of fish in need thereof, comprising administering to the fish an effective amount of a medicated fish feed. The medicated fish feed comprises fish feed granules or pellets coated with a composition comprising a neonicotinoid such as imidacloprid and a carrier having a high apparent digestibility coefficient such as a processed/cooked corn protein concentrate.

17 Claims, No Drawings

FISH FEED COMPOSITIONS CONTAINING A NEONICOTINOID FOR PREVENTING AND TREATING PARASITE INFECTIONS

CROSS-REFERENCE TO RELATED APPLICATIONS

The present application is a national phase entry of PCT Patent Application No. PCT/IB2015/054749, filed Jun. 24, 2015, which claims the benefit of U.S. provisional application No. 62/016,389 filed on Jun. 24, 2014, the contents of which are incorporated herein by reference in their entirety.

FIELD

The invention relates to new compositions and treatments using the neonicotinoid class of insecticides. For example, the invention relates to new medicated fish feeds comprising imidacloprid and methods and uses of the same for preventing or treating parasite infection in a plurality of fish.

BACKGROUND

Parasites in animals such as fish may, for example, cause animal suffering, significant expense and inconvenience to farmers. Drugs and pesticides are the typical treatment for parasites; however, this raises other issues. In feedstock animals, drugs are typically administered orally or topically to control the parasite. The drugs, and their metabolites, can then enter the food supply and the environment. Therefore, drugs are used sparingly and cautiously.

The salmon farming industry began in Norway in the early 1970's. The early sites were in sheltered areas in the Fjords along the coast of Norway. The diets were fish-based and made on site daily.

As the salmon farming industry grew, it began to take on many similarities with terrestrial agriculture (land farming). Salmon were enclosed in large numbers on commercial fish farms and became valuable and it could be observed when they exhibited diseases or parasite infections. Some products used to control diseases and parasite infections in terrestrial farming were then used to help salmon. For example, medicated pre-mixes used in terrestrial animal feeds such as oxytetracycline (an antibiotic used to treat bacterial infections) and ivermectin (used to treat parasites) were added to salmon feeds.

The aquaculture industry found that some of these medications were destroyed in the manufacturing of the extruded fish feed. Extrusion of fish feed involves mixing the ingredients of fish feed and then applying heat and pressure to this mixture so that it is extruded through dies. Extrusion processing, can be defined as thermo-mechanical treatment by which moistened, expansible, starch and/or proteinous materials are plasticized and cooked in a tube by a combination of moisture, pressure, temperature and mechanical shear, and then shaped through the die opening at an extruder outlet.

Temperatures of 100 Celsius and above are typically needed to have the fish feed expand after it goes through the extruder dye. This extremely hot fish feed comes out of the extruder and expands so that it then sinks slowly in water or even floats so fish have a significant amount of time to consume it.

It became practice for veterinarians to calculate the amount of medication required for the salmon and then direct the feed manufacturing plants to add, for example, 5% more medication to compensate for extruder loss. Extruder loss as used herein means destruction of some of the medication when the fish feed was being made in the extrusion process.

Sea lice genera *Lepeophtheirus* and *Caligus* are examples of salt water ectoparasitic copepods that are often treated with the drug named emamectin benzoate. In addition to the usual issues associated with the use of drugs, sea lice have recently appeared to become increasingly resistant to the drug (see, for example, Tools to Resolve Environmental Impacts and Treatment Resistance in Sea Lice, Dr. Mark Fast, Canadian Aquaculture R&D Review 2013). Therefore, there remains a need to identify new treatments for sea lice.

Neonicotinoids are generally known for certain types of insect control. U.S. Pat. No. 5,504,081 is entitled combating fish parasites. The patent abstract discloses the use of agonists and antagonists of the nicotinic acetylcholine receptors of insects for combating fish parasites. Several modes of administration are generally suggested in this patent, but not demonstrated in working examples. The only specific working examples in this patent in regards to treating a parasite of fish is in vitro tests treating sea lice by bathing, which is difficult in aquaculture where fish are often kept in the ocean. Bath treatments in tarps around sea cages can have errors in volume and become too diluted and lose effectiveness, and they also have to be so high in concentration that their killing effect is delivered in the 20 to 60 minute bath time. The chemical in the bath quickly enters the environment when tarps are released or well boats discharge their bath treatments. As well, residual pesticides or drugs may remain present even when treatment is no longer desired. Another big challenge to bath treatments has been incomplete mixing in tarped sea cages and fish avoiding the high concentration areas of an added pesticide that then results in poor lice control. U.S. Pat. No. 5,504,081 does not address determination of a minimum effective dose to avoid impacts on food supply and the environment. U.S. Pat. No. 5,504,081 columns 9-10 describe tests against salmon lice with bath dosages of 1 and 100 ppm of active substance. The 100 ppm bath, that kills 100% of the lice in one hour, would require, in a cubic meter of water, 1,000 liters; the usage of 100,000 milligrams of active imidacloprid ingredient going into the ocean.

PCT Patent Application Publication No. 2014/064184 relates to the use of clothianidin for controlling sea lice in a fish population. In the working examples of WO 2014/064184, Atlantic salmon infected with *L. salmonis* were given acetamiprid, clothianidin, imidacloprid and nitenpyram (1, 5 or 10 mg/kg/day for 7 days) as an in-feed treatment. WO 2014/064184 teaches that the results obtained reveal that acetamiprid and imidacloprid are unsuited for an in-feed treatment of salmon, as the food uptake at medium and higher concentrations of added active ingredient in the food is reduced to an unacceptable level and that clothianidin was shown to be the only active ingredient which provided full sea lice elimination while not affecting the feed uptake.

SUMMARY OF THE INVENTION

The present inventors have discovered that the carriers used in many pre-mixes for salmon are insufficient to ensure adequate consumption/absorption of neonicotinoids and that by using a carrier in the pre-mix that respects the salmon's digestive system, superior consumption and absorption of neonicotinoids at medium and high dosages may be obtained which is useful for example, for sea lice control in Atlantic salmon. The medicated feeds prepared in the present studies using such a pre-mix showed high sea lice removal and low wastage of feed.

Accordingly, the present disclosure includes a use of a medicated fish feed for preventing or treating parasite infection in a plurality of fish in need thereof, the medicated fish feed comprising fish feed granules or pellets coated with a composition comprising a neonicotinoid and a carrier having a high apparent digestibility coefficient.

In an embodiment, the neonicotinoid comprises imidacloprid, acetamiprid, dinotefuran, nitenpyram, thiacloprid, thiamethoxam or a veterinary acceptable salt of any of the foregoing. In another embodiment of the present disclosure, the concentration of active neonicotinoid in the composition is 11-90 wt %, 75-90 wt %, or 30-50 wt %, optionally 35-45 wt %, optionally at least 11 wt %, based on the total weight of the composition.

In an embodiment, the neonicotinoid is imidacloprid. In another embodiment, the concentration of active imidacloprid in the composition is 40 wt %, based on the total weight of the composition.

In an embodiment, the carrier comprises fish oil, fish meal, shrimp or krill meals or oils, poultry meal, processed/cooked protein concentrate (optionally a processed/cooked corn protein concentrate or a processed/cooked soybean protein concentrate), select amino acids, water or combinations thereof. In another embodiment, the carrier comprises a processed/cooked corn protein concentrate. In a further embodiment, the carrier further comprises fish oil.

In an embodiment, the medicated fish feed is for oral use by feeding a divided dose in a plurality of feeds daily over a dosage period of at least 3-6 days, optionally at least 3, 4 or 5 days and up to 10 days, optionally wherein the medicated fish feed is for oral use by feeding a divided dose in a plurality of feeds once every 3 to 4 days for up to 10 days.

In an embodiment, the daily dose comprises at least 4 mg/kg, optionally from 4 to 12 mg/kg. In another embodiment, the total dose comprises at least 20 mg/kg, optionally from 20 to 70 mg/kg.

In an embodiment, the fish is salmon. In another embodiment of the present disclosure, each salmon has an average mass of less than or equal to 5 kg, optionally an average mass of from 50 g to 5 kg.

In an embodiment, the parasite is sea lice, optionally pre-adult sea lice. In another embodiment of the present disclosure, the sea lice is *Lepeophtheirus* or *Caligus*, optionally *Lepeophtheirus salmonis*.

In an embodiment, after use, the fish are held in a pen prior to harvesting for the minimum time necessary for the neonicotinoid residue (optionally imidacloprid residue) to be reduced to a level that the fish is suitable for human consumption, optionally until residue testing on fish determines that the neonicotinoid residue in the fish is below 0.02 parts per million.

In another embodiment of the present disclosure, the fish are harvested, optionally wherein the fish are harvested 21, 22, 23, 24 or 25 days after the use is completed, optionally when neonicotinoid residue (optionally imidacloprid residue) in the fish is below 0.02 parts per million.

The present disclosure also includes a medicated fish feed comprising fish feed granules or pellets coated with a composition comprising a neonicotinoid and a carrier having a high apparent digestibility coefficient.

The present disclosure also includes a pre-mix composition for medicated fish feed comprising a neonicotinoid and a carrier having a high apparent digestibility coefficient.

The disclosure also includes a method for preventing or treating parasite infections in a plurality of fish in need thereof by administration of imidacloprid to the fish, the method comprising:

feeding (i.e. orally administering) to the fish, each day for at least 3, 4 or 5 days, a fish feed composition, the composition comprising a total imidacloprid daily dose averaging about: 3-7 mg/kg, optionally 4 mg or 5 mg of imidacloprid per kg of fish per day. The total dose over a five day total treatment period would typically be 15-35, optionally 18-30 mg, optionally 18-22, optionally 20 mg, of imidacloprid per kg of fish. These same total dose amounts may be administered over a shorter dosage period such as 4 days, or a longer dosage period, such as 6 days. One of skill in the art would appreciate that a veterinary acceptable imidacloprid salt could alternatively be administered. The total imidacloprid daily dose is optionally fed to the fish as a series of divided daily doses optionally comprising at least 2, 3, 4 or 5 feedings per day. After the total treatment period is complete (i.e. after the oral administration is complete for the desired number of days), the fish are typically held in the pen until imidacloprid residue decreases to a level that the fish are suitable for human consumption, e.g. less than 0.02 ppm in the fish. The method is effective to prevent or treat (reduce or eliminate) the parasite infection. Treatment typically achieves at least 90% removal for significant control of parasite, however, optionally 100% removal of the lice is achieved and it represents complete control of the parasite.

The present disclosure also includes a fish feed composition (i.e. a fish feed or a fish feed additive) comprising imidacloprid in a dosage described in this disclosure. The present disclosure also includes a use of imidacloprid for preventing or treating sea lice in fish, wherein the imidacloprid is administered in a composition described in this disclosure. The present disclosure also includes a kit for preparing a medicated fish feed for reducing or treating parasites in a fish population, comprising a supply of imidacloprid or a salt thereof in a container, and printed instructions for feeding the imidacloprid at a daily dose per kg of fish biomass per day for a total number of days of dosage period as described herein. The treated fish is optionally a salmon, such as an Atlantic salmon or Pacific salmon, or rainbow trout (*Oncorhynchus mykiss*). It will be appreciated by a person skilled in the art that any fish in need of prevention or treatment of infection could receive the compositions described herein, including the list of fish in U.S. Pat. No. 5,504,081 columns 5 and 6, and for prevention or treatment of a wide variety of parasites including the genera of parasites listed in column 5 of U.S. Pat. No. 5,504,081, and the foregoing is incorporated herein by reference.

DETAILED DESCRIPTION

The disclosure relates to compositions and methods of using the neonicotinoid class of insecticides in fish feed to control parasites, typically salt water crustacean parasites. Optionally, certain freshwater parasites may also be treated. This class of products includes, but is not limited to, the compounds imidacloprid, acetamiprid, dinotefuran, nitenpyram, thiacloprid, and thiamethoxam. These insecticides control the pest, such as sea lice, by impairing the nervous system of insects and crustaceans.

I. Methods and Uses

The present inventors disclose that feeding imidacloprid to fish in the form of a suitable medicated fish feed decreases parasite infestations (e.g. sea lice infections) and maintains good food uptake even at doses of 4 mg/kg/day and higher.

The medicated fish feed used in the studies of the present disclosure was prepared by mixing Empyreal™ 75, a corn protein concentrate with imidacloprid to form a premix then adding this premix to salmon feed using fish oil to help coat it onto the pellets of the salmon feed.

Accordingly, the present disclosure includes a method of preventing or treating parasite infection in a plurality of fish in need thereof, comprising administering to the fish an effective amount of a medicated fish feed, the medicated fish feed comprising fish feed granules or pellets coated with a composition comprising a neonicotinoid and a carrier having a high apparent digestibility coefficient. The present disclosure also includes a use of a medicated fish feed for preventing or treating parasite infection in a plurality of fish in need thereof, the medicated fish feed comprising fish feed granules or pellets coated with a composition comprising a neonicotinoid and a carrier having a high apparent digestibility coefficient. The present disclosure further includes a use of a neonicotinoid and a carrier having a high apparent digestibility coefficient for the preparation of a medicated fish feed for preventing or treating parasite infection in a plurality of fish in need thereof, the medicated fish feed comprising fish feed granules or pellets coated with a composition comprising the neonicotinoid and the carrier having a high apparent digestibility coefficient. The present disclosure yet further includes a medicated fish feed for use for preventing or treating parasite infection in a plurality of fish in need thereof, the medicated fish feed comprising fish feed granules or pellets coated with a composition comprising a neonicotinoid and a carrier having a high apparent digestibility coefficient.

In an embodiment, the neonicotinoid comprises, consists essentially of or consists of imidacloprid, acetamiprid, dinotefuran, nitenpyram, thiacloprid, thiamethoxam or a veterinary acceptable salt of any of the foregoing. In another embodiment, the neonicotinoid is imidacloprid. Optionally, the neonicotinoid comprises, consists essentially of or consists of nithiazine or a veterinary acceptable salt thereof.

Imidacloprid was the first commercialized member of a new class of insecticides known as neonicotinoids made by Bayer in 1986. Imidacloprid is also referred to as (2E)-1-((6-chloropyridin-3-yl)methyl)-N-nitroimidazolidin-2-imine, EC No: 428-040-8 and CAS No. 138261-41-3.

Imidacloprid is produced in a variety of concentrations with each batch having a range of active ingredient. To have a product that is consistent and easy to be added to fish feed, a consistent concentration of active ingredient is used. The activity level of imidacloprid is readily determined. For example, a purchased quantity of imidacloprid may state it is 95% active imidacloprid but on testing it may actually have an assay level of 97.1% active. A person skilled in the art can readily determine how much imidacloprid to mix with the carrier having a high apparent digestibility coefficient to provide a pre-mix composition having a particular percentage of active imidacloprid. For example, in an embodiment of the invention, the activity level of imidacloprid is first determined then the imidacloprid is mixed with Empyreal™ 75, a corn protein concentrate, to give a pre-mix comprising 40% active imidacloprid which is 400 grams of active imidacloprid per kilogram of pre-mix composition.

The concentration of active neonicotinoid in the composition can be any suitable concentration. While the studies of the present disclosure used an active concentration of imidacloprid of 40 wt %, a pre-mix active concentration other than 40 wt % could be used if desired. For example, 0.2 wt % active imidacloprid could be used but then this, may, for example, require shipping a lot of dilute medication. A 95 wt % active composition could also be used, but then this may mean there is not enough quantity of material to get an even mix on the fish feed so various concentrations in different parts of the feed are present which may translate to ranges in dosages eaten by fish and then wide ranges in efficacy and residues in the fish. The selection of a suitable concentration of active neonicotinoid can be made by a person skilled in the art. Optionally, the concentration of active neonicotinoid in the composition is at least 11 wt %, based on the total weight of the composition. In another embodiment, the concentration of active neonicotinoid in the composition is 11-90 wt %, 75-90 wt % or 30-50 wt %, based on the total weight of the composition. Optionally, the concentration of active neonicotinoid in the composition is 35-45 wt %, for example, 40 wt %, based on the total weight of the composition. In another embodiment, the neonicotinoid is imidacloprid and the concentration of active imidacloprid in the composition is 40 wt %, based on the total weight of the composition.

The carrier that has a high apparent digestibility coefficient (ADC) can be any suitable carrier that has a high apparent digestibility coefficient. For example, suitable carriers that have a high apparent digestibility coefficient are ones that do not contain a high amount of unprocessed starches or other products that are not very digestible by carnivorous fish such as salmon. The term "apparent digestibility coefficient" or the abbreviation "ADC" as used herein refers to the percentage of the quantity of food ingested which is not excreted as faeces. The ADC can be determined by a person skilled in the art using known methods (see, for example the method used by Mabrouk, H. A. and H. M. Nour, Assessment of apparent digestibility coefficients (ADCs %) of some animal protein sources by Gilthead Sea bream (*Sparus aurata*) *Egyptian Journal of Aquatic Research*, 2011, 37(2), 191-197). The term "high apparent digestibility coefficient" as used herein refers, for example, to an ADC of at least 90%.

Examples of suitable carriers that have a high apparent digestibility coefficient include fish oil, fish meal, shrimp or krill meals or oils, poultry meal, processed/cooked protein concentrate (for example, a processed/cooked corn protein concentrate or a processed/cooked soybean protein concentrate), select amino acids, water, combinations thereof or any other component of fish feed that has a high apparent digestibility coefficient.

In an embodiment, the carrier comprises a processed/cooked protein concentrate such as a processed/cooked corn protein concentrate. The selection of a suitable processed/cooked protein concentrate such as a processed/cooked corn protein concentrate can be made by a person skilled in the art. For example, processes for contacting a protein material with one or more wet-mill streams to increase the protein content of the protein containing material are disclosed in PCT Application Publication No. 2005/074704. For example, the processed/cooked protein concentrate can also be a corn protein concentrate as that term is used in Canadian Patent No. 2,617,908.

In an embodiment, the processed/cooked protein concentrate such as a processed/cooked corn protein concentrate comprises at least 80%, 85%, 90%, 95% or 99% protein, on a dry weight basis. In another embodiment, the processed/cooked protein concentrate such as a processed/cooked corn protein concentrate comprises less than 1% starch on a dry weight basis. Optionally, the processed/cooked protein concentrate such as a processed/cooked corn protein concentrate comprises at least 75.0% crude protein, at least 2.0% fat, at most 2.5% fiber and at most 1.0% starch, on a dry weight basis. For example, the processed/cooked corn protein concentrate is Empyreal™ 75.

In another embodiment, the carrier further comprises fish oil.

The selection of a suitable means to mix the neonicotinoid and the carrier having a high apparent digestibility coefficient can be made by a person skilled in the art. Then, for example, to formulate and administer the composition, a suitable amount (e.g. 5 kilograms) of the neonicotinoid (e.g. imidacloprid) containing pre-mix composition is mixed with a suitable amount (e.g. 5,000 kilogram) of fish feed and fed to the fish as the sole diet for 5 days. Optionally, a dry pre-mix composition is mixed in fish oil then applied to the fish feed, optionally in a vacuumed fat applicator. A vacuumed fat applicator is a commonly used apparatus in large fish feed making plants.

It will be appreciated by a person skilled in the art that some large clumps of the imidacloprid material may occur during the mixing process. For example, in the present studies, after mixing a 30 kg batch for 15 minutes in a drum, some lumps remained. The lumps were screened (also removing the larger Empyreal 75 particles), put back into powder form using a food blender, and then added back into the drum with the non-lumped material. The drum was then mixed for an additional 15 minutes. After the mixing period, no lumps were visible and the mix appeared quite homogenized.

The fish feed granules or pellets can be any suitable fish feed granules or pellets, the selection of which can be made by a person skilled in the art.

In the methods and uses of the present disclosure, an effective amount of the medicated fish feed is administered to the fish, optionally in a single administration, or preferably comprising a series of administrations. For example, the medicated fish feed is administered to the fish over a dosage period of at least 3-6 days, optionally at least 3, 4 or 5 days and up to 10 days.

Multiple feedings in fish (i.e. a divided daily dose) is expected to maintain levels in the fish better than a single daily dose. For example, in rats, 90% of radio-labeled imidacloprid is excreted in 24 hours. Fast excretion of imidacloprid in fish also occurs, as evidenced by the rapid depletion of residues in fish flesh. Therefore, multiple dosages per day over a number of days are typically used to keep imidacloprid levels high in the fish to kill the sea lice. Alternatively, for example, in farms having a colder water temperature, the dose is administered once per day. It will be appreciated by a person skilled in the art that a higher spike of medication can be obtained from such an administration.

Optionally, in the methods of the present disclosure, the medicated fish feed is orally administered to the fish by feeding a divided dose in a plurality of feeds daily over a dosage period of at least 3-6 days, optionally at least 3, 4 or 5 days and up to 10 days, optionally wherein the medicated fish feed is orally administered to the fish by feeding a divided dose in a plurality of feeds once every 3 to 4 days for up to 10 days. Optionally, in the uses of the present disclosure, The medicated fish feed is for oral use by feeding a divided dose in a plurality of feeds daily over a dosage period of at least 3-6 days, optionally at least 3, 4 or 5 days and up to 10 days, optionally wherein the medicated fish feed is for oral use by feeding a divided dose in a plurality of feeds once every 3 to 4 days for up to 10 days.

One of skill in the art can adjust dosage as necessary, for example adjusting on a per kilogram basis so the desired dose is measured and administered on an amount per kilogram of fish. Optionally, 3-7 mg/kg, such as 4, 5 or 6 mg/kg of fish, is administered per day. In another embodiment of the present disclosure, the daily dose comprises at least 1 mg/kg. For example, at least 2 mg/kg/day, optionally 2 mg/kg/day is administered/used every day for 5 days, at least 1.5 mg/kg/day, for example, 1.5 mg/kg/day is administered/used every day for 7 days or at least 1.1 mg/kg/day, for example, 1.1 to 1.5 mg/kg/day is administered/used every day for 10 days. In another embodiment, the daily dose comprises at least 4 mg/kg, optionally from 4 to 12 mg/kg, for example, the daily dose comprises 4 mg/kg, 8 mg/kg, 10 mg/kg or 12 mg/kg. In a further embodiment of the present disclosure, the total dose comprises at least 20 mg/kg, optionally from 20 to 70 mg/kg or 20 to 60 mg/kg, for example the total dose comprises 20 mg/kg, 40 mg/kg, 60 mg/kg or 70 mg/kg.

Medicated feed for fish is typically prepared based on the amount of feed that the fish are consuming each day.

For example, 20 milligrams of 40 wt % imidacloprid per kilogram of fish dosage divided over 5 days of feeding, if used in a sea cage site, would use 4 milligrams of active imidacloprid per day for five days. A total biomass of 100,000 kilograms multiplied by 20 milligrams is 2,000,000 milligrams of active imidacloprid required over 5 days. This equals 2,000 grams of active imidacloprid used. Since one kilogram of pre-mix composition may provide 400 grams of imidacloprid, 5 kilograms of premix is added to the fish feed.

One of skill in the art will appreciate the administered amount is a target dose. The actual dose received by an individual fish depends on consumption by the fish. In a salmon pen, when feeding medicated feed, some fish eat more and grow quicker so they will be receiving a bit higher dosage than a slower growing fish. If 100,000 kilograms of fish are eating on average approximately 1% of their body weight per day in fish feed and the medication is divided out over 5 days, then 5,000 kilograms of fish feed is to be used to deliver the desired dose. One of skill in the art will understand how to manage dosage in fish. In the feed trials described below, certain fish were fed approximately 4 milligrams of active imidacloprid, per kilogram of fish, per day for 5 days which gives a total dose of 20 milligrams per kilogram. Fish varied their consumption of feed by 1.1% to 1.43% per day which would be a variation of 26% consumption per day. In addition, one tank ate 97% of its medicated feed so it received an actual consumed dose 19.4 mg/kg and the other tank ate 91.66% so it received an actual consumed dose of 18.33 mg/kg of a total target dose of 20 mg/kg (4 mg/kg per day for 5 days). Therefore, the actual consumed dose by fish may optionally vary by approximately 20% of the target dose.

Salmon and other types of fish (e.g. the list of fish in U.S. Pat. No. 5,504,081 columns 5 and 6) are effectively treated with the compositions. The salmon are optionally Atlantic salmon (*Salmo salar*) or Pacific salmon of which there are 5 different species. The compositions could also be useful to treat sea lice infections in Halibut. In an embodiment, the fish is salmon. In another embodiment of the present disclosure, each fish (e.g. salmon) has an average mass of less than or equal to 5 kg, optionally an average mass of from 50 g to 5 kg.

For example, the neonicotinoid-containing medicated fish feed can treat sea lice infections. Other parasites including the genera of parasites listed in column 5 of U.S. Pat. No. 5,504,081 can be treated by such medicated fish feed. In an embodiment, the parasite is sea lice, optionally pre-adult sea lice. Optionally, the sea lice is *Lepeophtheirus* or *Caligus*, optionally *Lepeophtheirus salmonis*.

The present invention prevents and treats parasite infections with reduced environmental impact compared to treatment baths. In a cubic meter of water in a sea cage there is typically a maximum of 18 kilograms of fish. Optional embodiments of the compositions readily treat fish, through the fish feed, with an orally administered dosage averaging 4 milligrams of active imidacloprid per kilogram of fish per day for 5 days which is a total of 20 milligrams per kilogram of fish. References to a kg of fish should be understood as references to a kg of fish biomass. References to "fish" should be understood as references to a population of fish, except where the context indicates that a single fish is intended. For 18 kilograms of fish this would be 360 milligrams of active imidacloprid material. Therefore, treating fish in the feed with an effective amount of neonicotinoid in a suitable oral dosage form would significantly reduce environmental exposure to this active ingredient versus the prior art example of a 100 ppm bath which would require 100,000 milligrams of active imidacloprid in a cubic meter of water to treat the same 18 kilograms of fish. The present invention also reduces environmental exposure to this active ingredient versus the prior art example where the medicated fish feed is not well consumed. The present disclosure also addresses the creation of residues in the fish from treatment and withdrawal times to ensure human safety in consuming the fish.

In embodiments of the present disclosure, the method or use further comprises, after administration or use, as the case may be, holding the fish in a pen prior to harvesting for the minimum time necessary for the neonicotinoid residue (optionally imidacloprid residue) to be reduced to a level that the fish is suitable for human consumption, optionally until residue testing on fish determines that the neonicotinoid residue in the fish is below 0.02 parts per million. In other embodiments of the present disclosure, the method or use further comprises harvesting the fish, optionally 21, 22, 23, 24 or 25 days after the administration or use, as the case may be, is completed, optionally when neonicotinoid residue (optionally imidacloprid residue) in the fish is below 0.02 parts per million. It will be appreciated by a person skilled in the art that residue levels acceptable for harvest and therefore holding times may vary between different countries. It will also be appreciated that lower water temperatures typically increase excretion times of medications in fish (i.e. at lower water temperatures fish typically excrete lower amounts of medication per day) so longer holding periods would be expected at lower temperatures. The selection of suitable holding times and residue levels can be made by a skilled person.

II. Medicated Fish Feed, Pre-Mix Compositions and Kits

The present inventors disclose that feeding imidacloprid to fish in the form of a suitable medicated fish feed decreases parasite infestations (e.g. sea lice infections) and maintains good food uptake even at doses of 4 mg/kg/day and higher. The medicated fish feed used in the studies of the present disclosure was prepared by mixing Empyreal™ 75, a corn protein concentrate with imidacloprid to form a premix then adding this premix to salmon feed using fish oil to help coat it onto the pellets of the salmon feed.

Accordingly, the present disclosure also includes medicated fish feed comprising fish feed granules or pellets coated with a composition comprising a neonicotinoid and a carrier having a high apparent digestibility coefficient. It will be appreciated by a person skilled in the art that embodiments relating, for example, to the neonicotinoid and the carrier in the medicated fish feeds of the present disclosure can be varied as detailed herein for the methods and uses of the present disclosure.

The present disclosure also includes a pre-mix composition for medicated fish feed comprising a neonicotinoid and a carrier having a high apparent digestibility coefficient. It will be appreciated by a person skilled in the art that embodiments relating, for example, to the neonicotinoid and the carrier in the pre-mix compositions of the present disclosure can be varied as detailed herein for the methods and uses of the present disclosure.

The present disclosure also includes a kit for preparing a medicated fish feed for preventing or treating parasites in a fish population, comprising a supply of a pre-mix composition of the present disclosure in a container, and printed instructions for mixing the pre-mix composition with fish feed granules or pellets in an amount such that the neonicotinoid such as imidacloprid in the pre-mix composition is fed to the fish at a daily dose per kg of fish biomass per day for a total number of days of dosage period as described herein.

The following non-limiting examples are illustrative of the present application:

EXAMPLES

Example 1: Feed Trials

I. Materials and Methods

Empyreal™ 75, a processed corn protein concentrate, was mixed with imidacloprid to form a pre-mix. This pre-mix was then added to salmon feeds using fish oil to help coat it onto the pellets to prepare the medicated feed.

Medicated feed for fish was prepared based on the amount of feed that the fish were consuming each day to give a total dosage to different tanks of fish of 10, 20, 40, 60 and 100 milligrams of active ingredient (imidacloprid) over a 5 day period. Experiments were run using total dosages given over 5 days of feeding. A 5 day period was used to provide efficacy, convenience and safety.

The fish used had an average weight of 69.9 to 161.8 grams per tank. Individual fish weights ranged from 62 to 188 grams.

II. Results and Discussion

Sea lice have a number of developmental stages on salmon of which two are pre-adults that do a lot of damage to the fish (e.g. *Lepeophtheirus* pre-adult I, *Lepeophtheirus* pre-adult II, *Caligus* pre-adult I, *Caligus* pre-adult II). Compositions were tested on the two pre-adult stages of *Lepeophtheirus*. The disclosed compositions are also useful for killing sea lice in the adult male and adult female and adult gravid female stage and the juvenile *chalimus* stages.

Experiments used total dosages of 10, 20, 40, 60 and 100 milligrams of the active ingredient imidacloprid per kilogram of fish. Table 1 shows a summary of the food consumption observed:

TABLE 1

| Feed Trial Number One | | |
|---|---|---|
| Dosage of Imidacloprid | | Medicated food |
| per day (mg/kg fish) | total[1] (mg/kg fish) | consumption over 5 days (%) |
| 0 (control) | 0 (control) | 99.05 |
| 0 (control) | 0 (control) | 98.94 |

TABLE 1-continued

| 4 | 20 | 97.01 |
|---|----|-------|
| 4 | 20 | 91.66 |
| 8 | 40 | 97.10 |
| 8 | 40 | 59.51[3] |
| 12 | 60 | 93.30 |
| 12 | 60 | 64.63[3] |

| Feed Trial Number Two[2] | | |
|---|---|---|
| Dosage of Imidacloprid | | |
| per day (mg/kg fish) | total[1] (mg/kg fish) | Dosage of Imidacloprid |
| 2 | 10 | 97.25 |
| 20 | 100 | 59.23 |

[1]Over five days.
[2]Used control tanks from first trial.
[3]Fish observed to not adapt well to small tank used in experiment.

Table 2 contains a summary of the parasite reductions observed:

TABLE 2

| Feed Trial Number One[1] | | | |
|---|---|---|---|
| Dosage of Imidacloprid | | Lice removed by 3 days after last | Lice removed by 11 days after last |
| per day (mg/kg fish) | total[2] (mg/kg fish) | day of treatment | day of treatment |
| 0 (control) | 0 (control) | lice increased by 12% | 12.24%[4] |
| 0 (control) | 0 (control) | 5%[4] | 44%[4] |
| 4 | 20 | 96.70% | 100% |
| 4 | 20 | 96.75% | 100% |
| 8 | 40 | 97.84% | 97.84% |
| 12 | 60 | 100% | 100% |

| Feed Trial Number Two[3] | | | |
|---|---|---|---|
| Dosage of Imidacloprid | | Lice removed by 2 days after last | Lice removed by 9 days after last |
| per day (mg/kg fish) | total[2] (mg/kg fish) | day of treatment | day of treatment |
| 2 | 10 | 64.28% | 77.67% |
| 20 | 100 | 88.37% | no data |

[1]Data for fish observed to not adapt well to small tank not included.
[2]Over five days.
[3]Used control tanks from first trial.
[4]Some lice were lost over time despite no treatment.

The fish that received the 10 milligrams total dose given over 5 days, that is 2 milligrams of active per day, ate 97.25% of their medicated feed and had 77.7% removal of pre-adult lice. Duplicate testing of the 20 milligrams per kilogram of fish, that is 4 milligrams active ingredient per day for 5 days, showed 100% removal of the pre-adult lice. The higher dosages trialed, 40, 60 and 100 milligrams also gave very effective removal of lice.

Control tanks ate 98.94% and 99.05% of their food. The fish on the 20 mg/kg total dosage in two different tanks ate 91.66 and 97.01% of their medicated feed, respectively. One tank of fish on the 40 mg/kg total dosage ate 97.10% of their food while the other tank ate 59.51% of their food. One tank of fish on the 60 mg/kg total dosage in one tank ate 93.30% of their food while the other tank ate 64.63% of their food. In a second trial with no controls, one tank of fish receiving a 100 mg/kg total dosage ate 59.23% and one tank of fish receiving a total dosage of at 10 mg/kg ate 97.25% of their medicated feed.

When fish were dosed at the 4 mg per kilogram per day dosage for five days (20 mg/kg through sea lice trials on pre adult lice), three days into the five-day treatment, 13.6% of the *Lepeophtheirus* lice were removed. Eight days after the treatment had started there was 96.75% removal of sea lice; and 16 days after treatment had started, there was 100% removal of lice. Residue testing on fish showed that the fish dropped below 0.02 parts per million of imidacloprid, (which is the maximum residue limit for this medication when used as a pesticide in eggs and muscle in Canada) 23 days after the treatment ended.

The tested fish were fed at five times the 20 mg/kg total dosage (i.e. 100 mg/kg total dosage) with no mortalities occurring. These fish given the 100 mg/kg total dosage also had no abnormalities detectable on histological examination of their organs that could be linked to the higher dosage rate.

In salmon net pen cages some fish are growing at a slower rate, for example, due to a slower growth rate or being lower on the hierarchy ladder for accessing food. The target dose must be adequate enough that these fish feeding at a lower rate still receive enough medication to kill the lice that are on them or otherwise they may act as a reservoir for lice to re-infect the cage of fish. This may, for example, result in more frequent treatments and thereby additional discharge of medication to the environment and more medication being put in fish that eventually are eaten by people. In addition, lice that are on fish that only receive a partial dosage of the medication may allow lice to develop resistance to the active ingredient. Then, these partially resistant lice may, for example, repopulate the cage which can eventually lead to highly resistant lice that cause treatment failures or the need to increase the dosage of medications to get clearance of the now more-resistant lice. Higher dosages for developed resistant lice would put more medication into the environment and more into food necessitating new longer withdraw times (i.e. longer hold times in the pen and more expense to the farmer). One of skill in the art will appreciate that with different rates of food consumption there will be variable dosage ingested by individual salmon and can select a suitable dosage.

Residues were tested in the treated fish and levels decreased below 0.02 ppm of imidacloprid and its two major metabolites, 5-hydroxy imidacloprid and imidacloprid olefin within 21 to 28 days after medication ended.

Many of the carriers for medications used in terrestrial farming are unprocessed wheat or other grains which have a flour consistency. The active ingredient is mixed into the carrier to form a pre-mix that is added to fish feeds. This unprocessed grain material has a high amount of uncooked complex carbohydrates i.e. starch which has very low digestibility in salmon. Salmon are carnivores and they are very limited in digesting unprocessed or uncooked complex carbohydrates. In the past, these carriers which are high in complex carbohydrates went through the extrusion process in making fish feeds and were essentially cooked making them much more digestible and tolerable in the salmon diet. Using an unprocessed wheat carrier mixed with the active ingredient to form a pre-mix may, for example, result in poorer consumption and digestion. Some fish feed manufacturers add extra attractants to medicated fish feed such as shrimp/krill meal or shrimp/krill oil to increase consumption of the medicated feed but, while not wishing to be limited by theory, the unprocessed starch component of this medicated pre-mix may still reduce absorption of the medication and leaves a slug of undigested/poorly digested unprocessed complex carbohydrates in the salmon's digestive tract causing the salmon to feel unwell and possibly reduce its feeding intake. The present inventors disclose that better consumption, digestion and/or absorption of medications can be obtained if they are combined with processed carriers. A factor in determining if an oral medication works well is dependent on it being absorbed in sufficient quantities to achieve a concentration that is delivered to the area it is needed to control a parasite or other infectious agent such as a bacteria.

In contrast to the results reported in WO 2014/064184, which teaches that acetamiprid and imidacloprid are unsuited for an in-feed treatment of salmon as the food uptake at medium and higher concentrations of added active ingredient in the food is reduced to an unacceptable level, good consumption of the medicated feed in salmon was observed. This facilitates delivery of an effective concentration of the active ingredient to the parasite and thus good parasite reductions were observed in the present studies.

While not wishing to be limited by theory, the carriers used in many premixes for salmon are insufficient to ensure adequate consumption/absorption of neonicotinoids such as imidacloprid. In contrast, by using a carrier such as the corn protein concentrate Empyreal 75 that respects the salmon's digestive system, increased consumption and absorption of neonicotinoids such as imidacloprid at medium and high dosages can be obtained which is useful for pest (e.g. sea lice) control in fish (e.g. Atlantic salmon).

In addition, similar results to those obtained for imidacloprid are expected with thiamethoxam, thiacloprid, acetamiprid, nitenpyram and dinotefuran. Accordingly, the medicated feed of the present disclosure may also be used to deliver other neonicotinoids for example, for sea louse control in salmon and other fish. Other types of neonicotinoids are useful in the formulations and doses described herein to prevent and treat parasite infection in fish.

While the present disclosure has been described with reference to what are presently considered to be the preferred examples, it is to be understood that the present disclosure is not limited to the disclosed examples. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

The invention claimed is:

1. A method for preventing or treating parasite infection in a plurality of fish, comprising administering to the fish in need thereof a medicated fish feed, wherein the medicated fish feed comprises fish feed granules or pellets coated with a composition comprising a neonicotinoid and a carrier having an apparent digestibility coefficient of at least 90%, wherein the neonicotinoid comprises imidacloprid or a veterinary acceptable salt thereof, wherein the carrier comprises a processed or cooked corn protein concentrate and fish oil, and wherein the fish feed is administered at a daily dose of at least 1.4 mg imidacloprid/kg fish (mg/kg), or a total dose of 10 to 70 mg/kg based on the daily dose per the entire treatment, wherein the parasite infection is lice infection in a plurality of fish, and wherein the method does not result in the death of the fish.

2. The method of claim 1, wherein the concentration of active neonicotinoid in the composition is 11-90 wt % based on the total weight of the composition.

3. The method of claim 1, wherein the concentration of active imidacloprid in the composition is 40 wt %, based on the total weight of the composition.

4. The method of claim 1, wherein the carrier further comprises fish meal, shrimp meal, krill meal, shrimp oil, krill oil, poultry meal, a processed or cooked soybean protein concentrate, water or combinations thereof.

5. The method of claim 1, wherein the administering step comprises orally administering the medicated fish feed by feeding a divided dose in a plurality of feeds daily over a dosage period of at least 3 days and up to 10 days, or wherein the medicated fish feed is for oral administration by feeding a divided dose in a plurality of feeds once every 3 or 4 days for up to 10 days.

6. The method of claim 1, wherein the fish is salmon.

7. The method of claim 6, wherein each salmon has an average mass of less than or equal to 5 kg.

8. The method of claim 1, wherein the lice on the fish is adult sea lice, or pre-adult sea lice.

9. The method of claim 8, wherein the sea lice is *Lepeophtheirus, Caligus,* or *Lepeophtheirus salmonis*.

10. The method of claim 1, wherein after the administering step, the fish are held in a pen prior to harvesting for the minimum time necessary for the neonicotinoid residue or imidacloprid residue to be reduced to a level that the fish is suitable for human consumption, or until residue testing on fish determines that the neonicotinoid residue in the fish is below 0.02 parts per million.

11. The method of claim 1, further comprising harvesting the fish 21, 22, 23, 24 or 25 days after the administering step is completed, or when imidacloprid residue in the fish is below 0.02 parts per million.

12. The method of claim 2, wherein the concentration of active neonicotinoid in the composition is 30-50 wt % based on the total weight of the composition.

13. The method of claim 5, wherein the feeding comprises feeding a divided dose in a plurality of feeds daily over a dosage period of at least 3, 4 or 5 days up to 10 days.

14. The method of claim 1, wherein the fish feed is administered at a daily dose of 1.4 to 12 mg/kg, or a total dose of 10 to 70 mg/kg per the entire treatment.

15. The method of claim 14, wherein the administering step comprises orally administering the medicated fish feed by feeding a divided dose in a plurality of feeds daily over a dosage period of 7 days, wherein the fish feed is administered at a daily dose of 1.4 mg to 3 mg/kg, and a total dose of 9.8 to 21 mg/kg per the entire treatment.

16. The method of claim 1, wherein the fish feed does not comprise wheat.

17. The method of claim 1, wherein the fish feed is administered at a total dose of 10 to 15 mg/kg per the entire treatment.

* * * * *